(12) United States Patent
Satyanarayana et al.

(10) Patent No.: US 7,615,762 B2
(45) Date of Patent: Nov. 10, 2009

(54) METHOD AND APPARATUS FOR LOW QUANTITY DETECTION OF BIOPARTICLES IN SMALL SAMPLE VOLUMES

(75) Inventors: Srinagesh Satyanarayana, Austin, TX (US); Sulatha Dwarakanath, Austin, TX (US)

(73) Assignee: Nano Science Diagnostics, Inc., Austin, TX (US)

( * ) Notice: Subject to any disclaimer, the term of this patent is extended or adjusted under 35 U.S.C. 154(b) by 190 days.

(21) Appl. No.: 11/292,604

(22) Filed: Dec. 2, 2005

(65) Prior Publication Data

US 2006/0219939 A1   Oct. 5, 2006

Related U.S. Application Data

(60) Provisional application No. 60/632,791, filed on Dec. 3, 2004.

(51) Int. Cl.
*G01N 21/64* (2006.01)
(52) U.S. Cl. .................. 250/461.2; 422/82.08
(58) Field of Classification Search ............ 250/458.1, 250/358.1, 361 R, 362, 363.01, 364, 365, 250/367, 361 C, 461.2, 459.1, 461.1; 204/155, 204/156, 157.15, 157.2; 422/63, 68.1, 70, 422/73, 81, 82.01, 82.05, 82.07, 82.08, 82
See application file for complete search history.

(56) References Cited

U.S. PATENT DOCUMENTS

| | | | |
|---|---|---|---|
| 4,390,403 A | 6/1983 | Batchelder | |
| 5,344,535 A | 9/1994 | Betts et al. | |
| 5,454,472 A | 10/1995 | Benecke et al. | |
| 5,605,662 A | 2/1997 | Heller et al. | |
| 5,632,957 A | 5/1997 | Heller et al. | |
| 5,993,631 A | 11/1999 | Parton et al. | |
| 6,056,861 A | 5/2000 | Fuhr et al. | |
| 6,149,789 A | 11/2000 | Benecke et al. | |

(Continued)

FOREIGN PATENT DOCUMENTS

WO   WO 98/41841 A1   9/1998

(Continued)

OTHER PUBLICATIONS

Cui L., Zhang T., Morgan H.; Optical Particle Detection Integrated in a Dielectrophoretic Lab-on-a-Chip; 2002; Journal of Micromechanics and Microengineering; vol. 12; pp. 7-12.*

(Continued)

*Primary Examiner*—David P Porta
*Assistant Examiner*—David S Baker
(74) *Attorney, Agent, or Firm*—Fish & Richardson P.C.; Ross Spencer Garsson

(57) ABSTRACT

A novel apparatus and method is described for detection of very small quantities (a few hundred molecules) of bioparticles in nanoliter/picoliter quantities of a sample. The apparatus involves a very small and low cost apparatus that contains a fluorometer. The detection process uses the fluorescence of nanoparticles. Dielectrophoresis is used to concentrate, mix and position the target particles with regard to the light sensor such that maximum detection efficiency is achieved. This allows low cost implementation of low cost point of care tests for disease (animal and plant), infection, food-borne bacteria detection, nucleotide sequencing and pathogen detection (bioterrorism) in real world applications.

17 Claims, 14 Drawing Sheets

U.S. PATENT DOCUMENTS

| | | | |
|---|---|---|---|
| 6,303,316 | B1 | 10/2001 | Kiel et al. |
| 6,417,423 | B1 | 7/2002 | Koper et al. |
| 6,541,617 | B1 | 4/2003 | Bamdad et al. |
| 6,569,630 | B1 | 5/2003 | Vivekananda et al. |
| 6,596,143 | B1 * | 7/2003 | Wang et al. ............... 204/547 |
| 6,680,377 | B1 | 1/2004 | Stanton et al. |
| 6,750,065 | B1 | 6/2004 | White et al. |
| 6,787,018 | B1 | 9/2004 | Miles et al. |
| 6,790,671 | B1 * | 9/2004 | Austin et al. ............... 436/172 |
| 6,824,664 | B1 * | 11/2004 | Austin et al. ............... 204/643 |
| 6,858,439 | B1 * | 2/2005 | Xu et al. ..................... 436/518 |
| 7,214,298 | B2 * | 5/2007 | Spence et al. ............... 204/450 |
| 7,452,726 | B2 * | 11/2008 | Chou et al. ................... 436/63 |
| 2002/0081714 | A1 | 6/2002 | Jain et al. |
| 2002/0155586 | A1 | 10/2002 | Cheng et al. |
| 2002/0187503 | A1 * | 12/2002 | Harrold et al. ................. 435/6 |
| 2003/0031090 | A1 * | 2/2003 | Ho et al. ..................... 366/341 |
| 2003/0108612 | A1 | 6/2003 | Xu et al. |
| 2003/0170613 | A1 | 9/2003 | Straus et al. |
| 2004/0077105 | A1 * | 4/2004 | Wu et al. ..................... 436/524 |
| 2004/0233424 | A1 | 11/2004 | Lee et al. |
| 2004/0253821 | A1 * | 12/2004 | Howitz et al. ............... 438/689 |
| 2005/0014146 | A1 * | 1/2005 | Manaresi et al. ............... 435/6 |
| 2005/0176029 | A1 * | 8/2005 | Heller et al. ................... 435/6 |
| 2005/0207940 | A1 * | 9/2005 | Butler et al. ................... 422/73 |
| 2006/0011862 | A1 * | 1/2006 | Bernstein ................. 250/461.2 |
| 2006/0131494 | A1 * | 6/2006 | Grier et al. ................. 250/251 |

FOREIGN PATENT DOCUMENTS

| | | |
|---|---|---|
| WO | WO 03014739 A1 | 2/2003 |
| WO | WO 03102126 A | 12/2003 |

OTHER PUBLICATIONS

Cummings E.B., Singh A.K.; Dielectrophoresis in Microchips Containing Arrays of Insulating Posts: Theoretical and Experimental Results; Sep. 15, 2003; Analytical Chemistry; vol. 75 No. 18; pp. 4724-4731.*

Nanoelectromechanics in engineering and biology, M.P. Hughes, CRC Press.

In situ assembly of Colloidal particles into miniaturized biosensors, O.D. Velev, and E.W. Kaler, Langmuir, vol. 15, No. 11, pp. 3693-3698, May 25, 1999.

Towards single molecule manipulation with dielectrophoresis using nanoelectrodes, L. Zheng, et. al., Proceedings of the 3rd IEEE Conference on Nanotechnology, 1, 437-440 (2003).

Control and modeling of the dielectrophoretic assembly of on-chip nanoparticle wires, K. H. Bhatt, O.D. Velev, Langmuir, Sep. 24, 2004, vol. 20, No. 2, pp. 467-476.

Working with FluoSpheres Fluorescent Microspheres, Jun. 2004, Molecular Probes, www.probes.com.

TD700 Laboratory fluorometer, www.turnerbiosystems.com.

Bruno J.G. and Kiel J.L., "Effect of radio-frequency radiation (RFR) and Diazoluminomelanin (DALM) on the growth potential of bacill," Electricity and Magnetism in Biology and Medicine, pp. 231-233 (1993) San Francisco Press.

Bruno J.G. and Kiel J.L., "In vitro selection of DNA aptamars to anthrax spores with electrochemiluminescence detection," Biosensors & Bioelectronics 14:457-464 (1999).

Bruno J.G. and Kiel J.L., "Use of magnetic beads in selection and detection of biotoxin aptamers by ECL and enzymatic methods," BioTechniques 32:178-183 (2002).

Bruno J.G. and May M.W., "A color image analysis method for assessment of germination based on differential fluorescence staining of bacterial spores and vegetative cells by acridine orange," Biotechnic. & Histochem. 70:175-184 (1995).

Bruno J.G., Ulvick S.J., Uzzell G.L., Tabb J.S., Valdes E.R., and Batt C.A., "Novel immuno-FRET assay method for Bacillus spores and *E. coli* O157:Hy" Biochem. Biophys. Res. Comm. 287:875-880 (2001).

Friedberg J.S., et al., "Antibody-targeted photolysis. Bacteriocidal effects of Sn(IV) chlorine e6- dextran-monoclonal antibody conjugates," Ann. N.Y. Acad. Sci. 618:383-393 (1991).

Gao X., Chan W.C., Nie S., "Quantum-dot nanocrystals for ultrasensitive biological labeling and multicolor optical encoding," J. Biomed. Opt. 7:532-537 (2002).

Harma H., Soukka T., Lovgren T., "Europium nanoparticles and time-resolved fluorescence for ultrasensitive detection of prostate-specific antigen," Clin. Chem. 47:561-568 (2001).

Hirsch L.R., et al., "Nanoshell-mediated near infrared thermal therapy of tumors under magnetic guidance," Proc. Natl. Acad. Sci., USA 100:13549-13554 (2003).

Jaiswal J.K., et al., "Long-term multiple color imaging of live cells using quantum dot bioconjugates," Nat. Biotechnol. 21:47-51 (2003).

Kirschvink J.L., "Microwave absorption by magnetite: a possible mechanism for coupling nonthermal levels of radiation to biological systems," Bioelectromagnetics. 17:187-194 (1996).

Kloepfer J.A., et al., "Quantum dots as strain and metabolism-specific microbiological labels," Applied and Environmental Microbiology, 69:4205-4213 (2003).

Pinnick RG., Hill S.C., et al. and Bruno, J.G., "Fluorescence particle counter for dectecting airborne bacteria and other biological particles," Aerosol Sci. Technol. 23:653-664 (1995).

Schaertl S., Meyer-Almes F.J., Lopez-Calle E., Siemers A., Kramer J., "A novel and robust homogeneous fluorescence-based assay using nanoparticles for pharmaceutical screening and diagnostics," J. Biomol. Screen. 5:227-238 (2000).

Soukka T., Paukkunen J., Harma H., Lonnberg S., Lindroos H., Lovgren T., "Supersensitive time-resolved immunofluorometric assay of free prostate-specific antigen with nanoparticle label technology," Clin. Chem. 47:1269-1278 (2001).

Van Sark W.G., Frederix P.L., Bol A.A., Gerritsen H.C., Meijerink A., "Blueing, bleaching and blinking of CdSe/ZnS quantum dots," Chemphyschem. 3:871-879 (2002).

Yu H. and Bruno J.G., "Immunomagnetic-electrochemiluminescent detection of *Escherichia colo* 1057 and *Salmonella typhimurium* in foods and environmental water samples," Appl. Environ. Microbiol. 62:587-592 (1996).

Dwarakanath, S., et al., "Quantum dot-antibody and aptamer conjugates shift fluorescence upon binding bateria," Biomedical and Biophysical Research Communications 325, pp. 739-743 (2004).

Da Silva, M.J. and Quivy, A.A., "Anomalous blueshift in vertically coupled InAs/GaAs quantum dots InGaAs strain-reducing layers," Brazilian Journal of Physics, vol. 32, No. 2A, pp. 290-292, Jun. 2002.

* cited by examiner

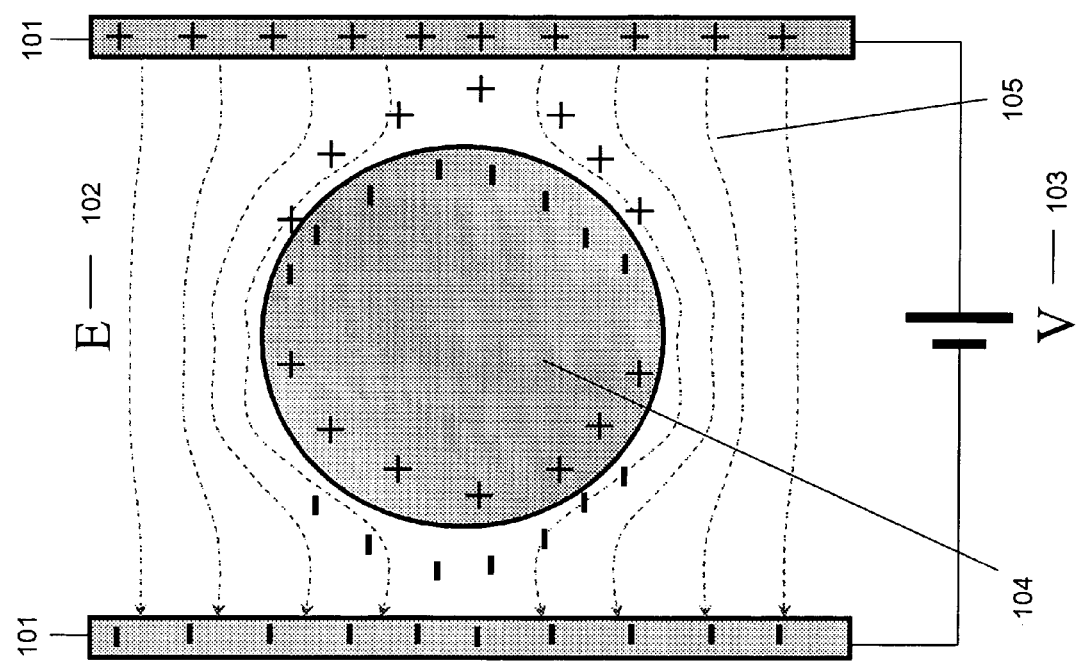

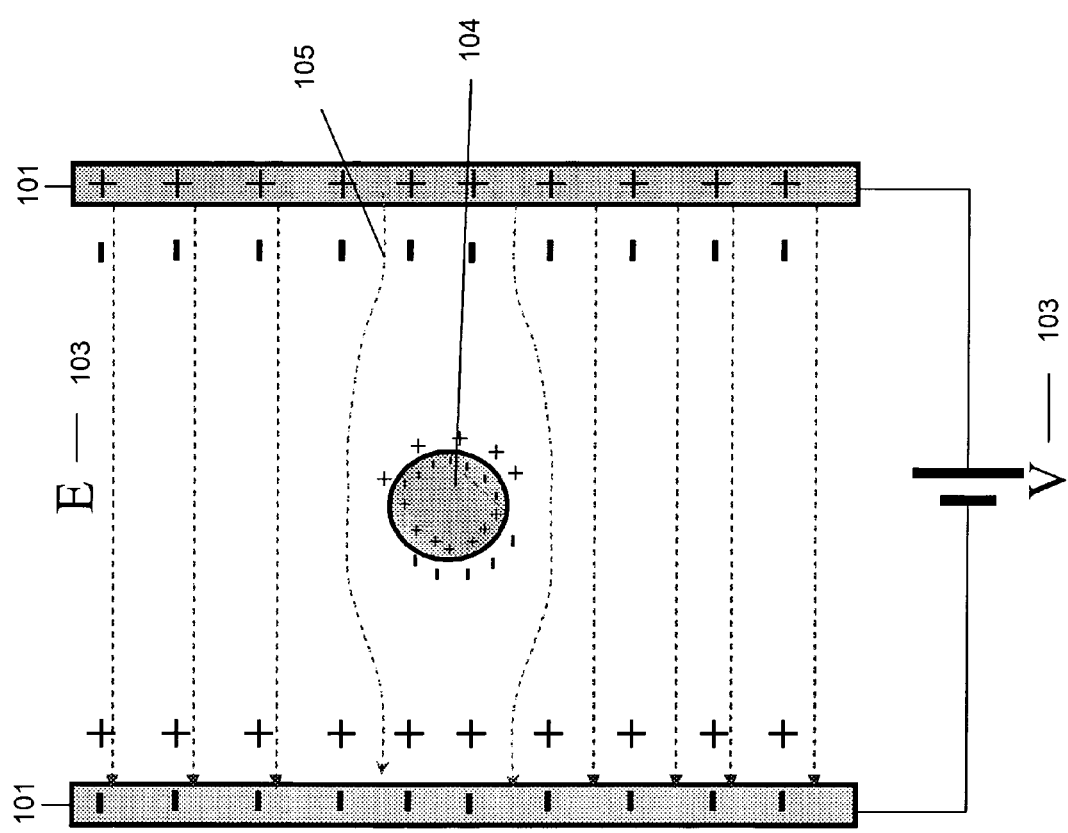

METHOD AND APPARATUS FOR LOW QUANTITY DETECTION OF BIOPARTICLES IN SMALL SAMPLE VOLUMES

This application claims benefit of U.S. Provisional Application No. 60/632,791, filed Dec. 3, 2004.

RELATED PATENT APPLICATION

U.S. patent application Ser. No. 11/222,093 filed Sep. 8, 2005, claiming priority to U.S. patent application No. 60/614,688 filed Sep. 30, 2004 entitled "Method for Detection and Decontamination of Antigens by Nanoparticle-Raman Spectroscopy" having Sulatha Dwarakanath et al. as inventors and assigned to the Assignee of the present invention, which patent application is attached hereto as Attachment A.

FIELD OF THE INVENTION

The field of the invention relates generally to the detection of bioparticles using dielectrophoresis.

BACKGROUND

There is a great need for low cost detection of bioparticles in various applications like disease diagnostics in animals and plants, bioterrorism, food inspection, and scientific research. Samples in such applications are found in a liquid medium. These particles can range from a few nanometers (nm) in size to a few micrometers (μm) in size. Viewing these particles with the naked eye is difficult. While μm size particles can be viewed with a microscope, nanometer (nm) scale particles require SEM, TEM, or AFM techniques. Techniques that involve the use of a microscope or SEM, TEM, AFM are not low cost in nature.

At a simple level, color change or light emission is usually an indicator of positive detection. Most low cost tests involve combining a few drops of a reagent with a sample on filter paper that has a color standard. If the target particle is detected with significant quantity, the reagent renders the color to a desired shade on the scale. While it would be nice to have all color change indicating reagents for detection, it is not always possible. In some cases the result of detection may involve multiple steps. For example, the target displays an antigen and a fluorescent-tagged antibody is then used to selectively bind to the target molecule. Following such a binding, excitation has to be provided to the combination for the fluorescence to indicate the presence of a valid target particle.

Another problem arises when a nanoliter drop sample has only a few of the target particles. In such cases, using color change as an indicator is impractical. Therefore a fluoro-tag may be used. However, having only a few molecules limits the number of photons emitted from the sample drop. Methods to solve this problem include: 1) increasing the light intensity of each fluoro-tag; 2) increasing the number of target molecules (by using a larger sample size and concentrating the sample drop); 3) using a higher sensitivity photodetector and 4) using other techniques like electrical conductivity change detection. While option 4 is viable only in a few cases, option 1 has been implemented in recent products by using nanoparticles that usually offer higher luminosity. In low cost diagnostic products, using photomultipliers to increase the photon counting efficiency or using complex optics and manual positioning are ruled out due to their increased cost.

Fluorescence Detection

Fluorescence microscopes are available from vendors like Perkin Elmer, Hitachi, Spec, etc. Smaller handheld fluorometers are available from Turner biosystems (16). Bench top models that use a bank of emission and excitation filters and multiple excitation sources to scan the spectrum from 200 nm to 1200 nm and provide a plot of the excitation and emission spectra are also available. The microscopes use a photomultiplier tube and focusing optics to increase the sensitivity and provide a field of view. All these instruments operate on the sample and reagent being present in a cuvette. None of them use dielectrophoresis (DEP) for manipulating the particles. Most of the fluorescent tags are latex beads (15) that have a fluorophore attached. These particles are relatively large in size (μm).

BRIEF SUMMARY OF THE INVENTION

An embodiment of the present invention is an apparatus for detection of bioparticles comprising an excitation source; a disposable sample holder comprising electrodes wherein the disposable sample holder is situated to receive output from the excitation source; a sample comprising bioparticles situated on the disposable sample holder; an AC voltage generator located in contact with the electrodes; and a photodetector disposed to receive fluorescence from the bioparticles on the disposable sample holder; wherein dielectrophoresis is used to concentrate bioparticles into the field of view of the photodetector.

In additional embodiments of the present invention, the apparatus may also further comprise one or more of the following: an excitation filter located between the excitation source and the sample, an emission filter located between the sample and the photodetector and a sample cover located between the sample and the photodetector. In a further embodiment of the present invention, a multiple electrode array may be used to bring a tagged bioparticle cluster into the field of view of the photodetector. In another embodiment of the present invention, the bioparticles are tagged bioparticles. In a further embodiment of the present invention, a fluorescent nanoparticle tagged with an antibody is used to detect bioparticles in the sample. In yet another embodiment of the present invention, a switching pattern is used to mix the sample. In another embodiment of the present invention, dielectrophoresis utilizes the proper crossover frequency so that only the tagged bioparticles move into the field of view of the photodetector.

Another embodiment of the present invention is a method for detection of bioparticles comprising adding a fluorescent nanoparticle tagged with an antibody to a sample; placing a sample comprising bioparticles upon a disposable sample holder; placing the disposable sample holder comprising electrodes in contact with an AC voltage generator; using dielectrophoresis to concentrate tagged bioparticles into the field of view of the photodetector; exposing the sample upon the disposable sample holder to an excitation source; and detecting fluorescence of the tagged bioparticles.

In additional embodiments of the present invention, the method may further comprise one or more of the following: using an excitation and an emission filter, an amplifier, covering the sample with a sample cover, using a multiple electrode array to bring a tagged bioparticle cluster into the field of view of the photodetector, using a switching pattern is used to mix the sample and selecting the proper crossover frequency so that only the fluorescent nanoparticle tagged bioparticles move into the field of view of the photodetector.

The foregoing has outlined rather broadly the features and technical advantages of a number of embodiments of the present invention in order that the detailed description of the present invention that follows may be better understood. Additional features and advantages of the invention will be described hereinafter.

BRIEF DESCRIPTION OF THE DRAWINGS

The foregoing summary as well as the following detailed description will be better understood when read in conjunction with the appended drawings. It should be understood, however, that the invention is not limited to the precise arrangements and instrumentalities shown herein. The components in the drawings are not necessarily to scale, emphasis instead being placed upon clearly illustrating the principles of the present invention. The invention may take physical form in certain parts and arrangement of parts. For a more complete understanding of the present invention, and the advantages thereof, reference is now made to the following descriptions taken in conjunction with the accompanying drawings, in which.

DETAILED DESCRIPTION

The threshold of detection of bioparticles can be improved using dielectrophoresis to move, mix and concentrate a few fluoro-tagged bioparticles into the field of view of the sensor that is small and does not have any focusing optics.

Dielectrophoresis

All particles in nature are made up of molecules. Molecules in turn have an electronic structure. In each particle (nanoparticle, virus, bacteria, cell, tagging antibody, antigen, DNA, RNA and protein) some molecules have loosely bound outer orbit electrons that are free to move about the confines of the particle. These are called free electrons. The degree of mobility of these electrons gives the particle a certain electrical conductivity. Metals have high conductivity, as these free electrons are very free and can be used to carry current. In semiconducting or insulating particles these free electrons allow an external electric field to convert the particle into a dipole. A dipole is a particle in which the free charge is not distributed uniformly. FIG. 1 shows a particle that has been rendered into a dipole by the application of an electric field. In semiconducting particles these can be called "loose electrons." These electrons cannot usually leave the confines of the particle. Most semiconducting particles have an insulating shell that maintains the charge and material integrity of the contents of the particle. Note that particles that dissolve in a liquid medium cannot be called bioparticles. Bioparticles are organic molecules (or a collection of molecules) like cells, bacteria, viruses, DNA, RNA, protein. Some come with a protective shield (cell wall, plasmid, etc.) Most bioparticles are dipoles.

Conducting particles in a liquid medium are of not much use, as these dipoles cannot be formed. Of interest are the semiconducting particles where "loose electrons" allow the rendering of a particle into a dipole by applying an electric field. Once the bioparticles have been rendered into dipoles, any gradient setup in the sample drop allows us to move the particles to the region of maximum or minimum electric field gradient.

FIG. 1 shows a bioparticle in an electric field. The electric field is applied by delivering a voltage across the two conducting plates.

Figure 1A:
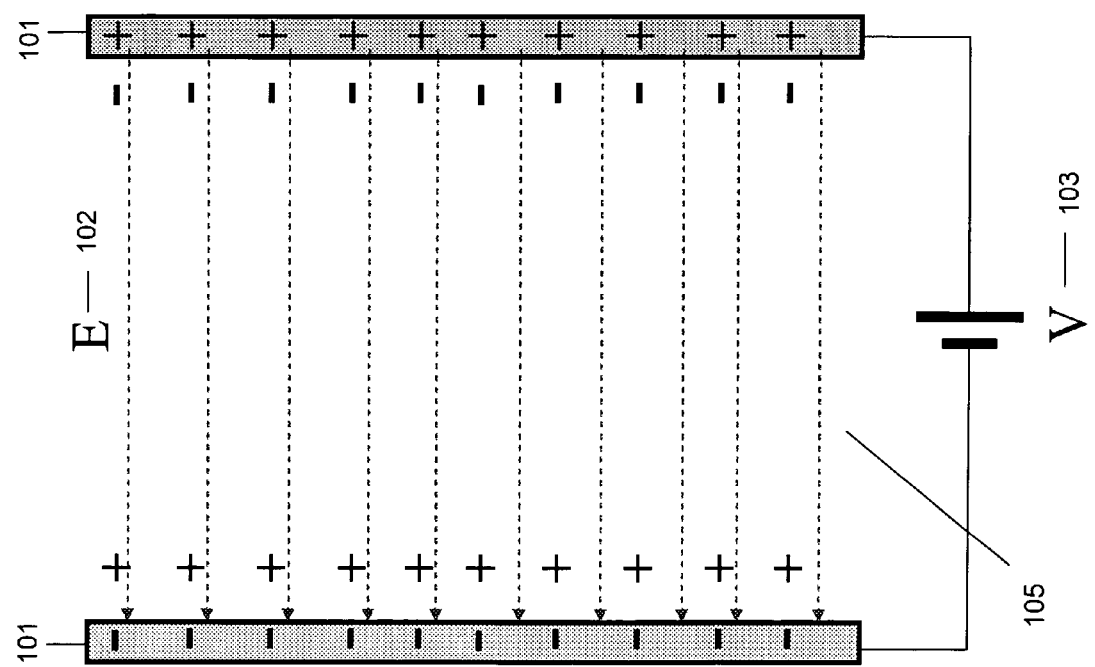
FIG. 1. (a) Uniform electric field (E) 102 applied to a medium using a voltage source 103. (b) Electric field 102 being distorted by the bioparticle 104. A dipole is created and the field lines 105 are distorted. Here the permittivity of the bioparticle 104 and the medium are different. (c) A more realistic rendering of the electrodes 101 and the bioparticle 104.
Figure 2:
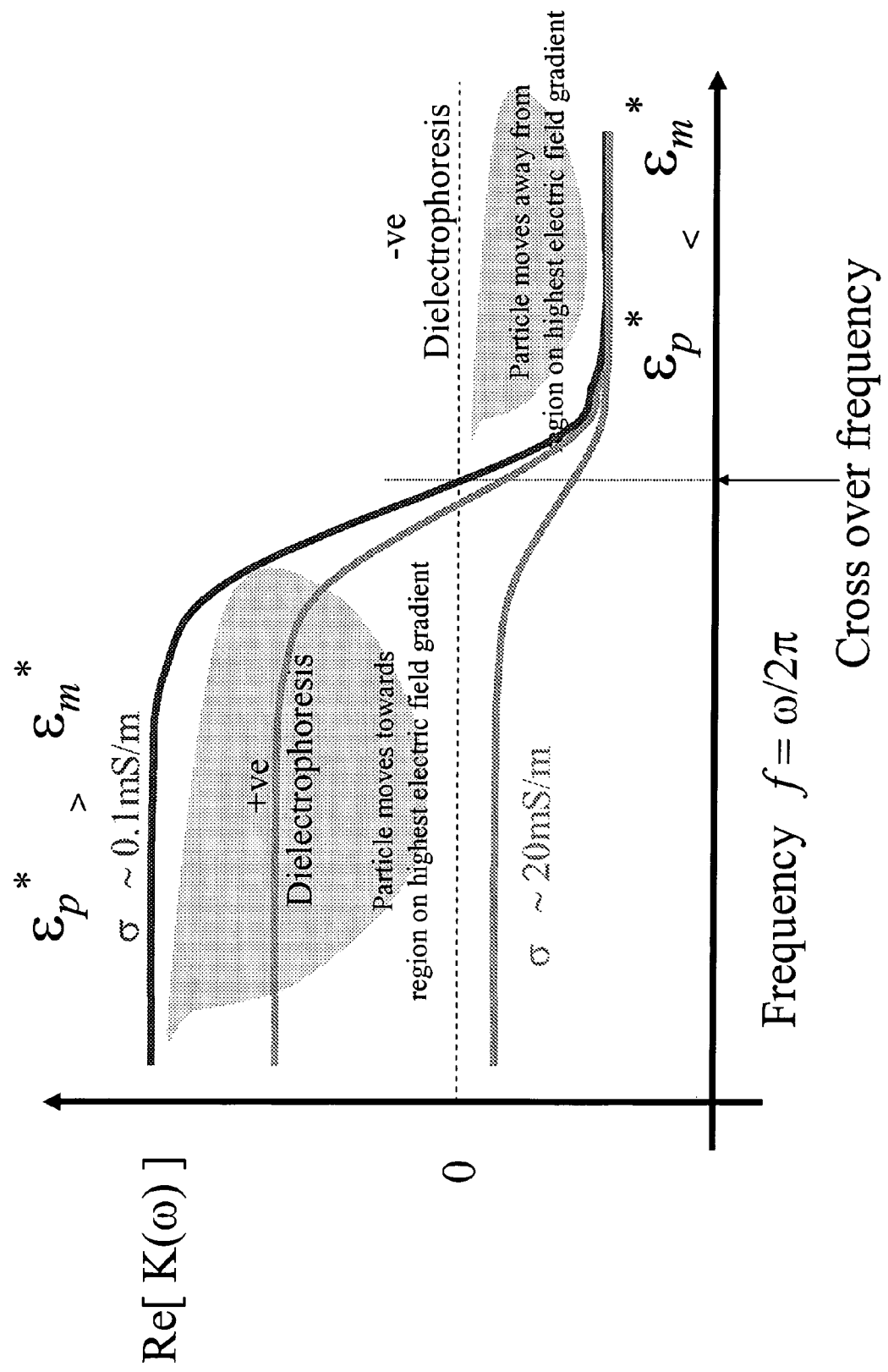
FIG. 2. Variation of the Charles Mosetti factor over frequency and the crossover frequency.

If the voltage is fixed then the electric field is uniform in the absence of the bioparticles (FIG. 1a). A bioparticle is introduced into the electric field, the medium and the particle having different permittivity and conductivities, causes the field lines to distort as shown in FIG. 1. Charges in the bioparticle and on its surface (from the medium) get rearranged as shown in FIG. 1b. Since there is a charge nonuniformity, the bioparticle will experience a force given by Eq. 1. The terms in the equation are explained below. The direction of motion depends on the relative permittivities of the particle and the medium. Particle size and electric field gradient play a role. Motion of the particle will depend on other impeding forces like gravity, viscosity and Brownian motion. These forces are usually negligible in the case of sub-micron particles. FIG. 2 shows a curve that describes the behavior of the K(w) term. Re[K(w)] refers to the real part of the K(w). K(w) is called the Charles Mosetti factor (10). K(w) is a complex number since the permittivities of the particle and medium are complex quantities.

$$F=4\pi r^3 \epsilon_m Re[K(\omega)]\nabla E^2 \qquad \text{Eq. 1.}$$

$\epsilon_p^*$ Particle's permitivity
$\epsilon_m^*$ Medium's permitivity
Re[K($\omega$)] Real part of Charles Mosetti factor =Re[($\epsilon_p^*-\epsilon_m^*$)/($\epsilon_p^*+2\epsilon_m^*$)]
f=$\omega/2\pi$ Frequency
$\nabla E^2$ Gradient of the Electric field E
r Radius of the particle (assuming it is spherical)

Complex quantities give us an extra degree of freedom to manipulate the direction of motion. As the frequency is changed, K(w) decreases, and the point where it crosses the zero point is called the crossover frequency. When K(w) changes sign, the force is reversed. The two regions of the curve are termed positive and negative dielectrophoresis regions (FIG. 2). While the upper curve represents a low/medium concentration, the curves below show K(w) for higher values of medium conductivity.

Figure 3:
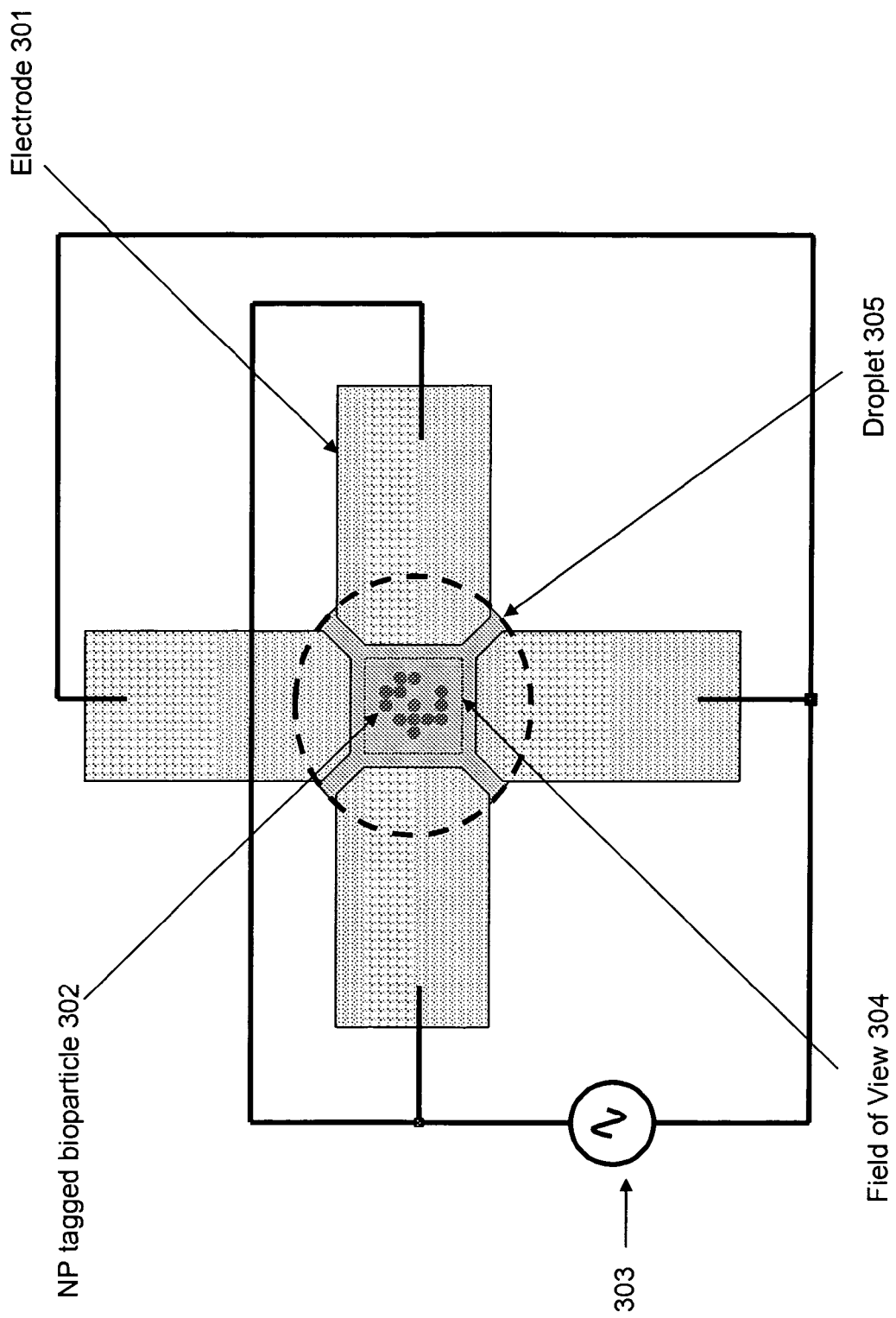
FIG. 3. The electrical setup for the electrodes 301 and the droplet 305 for performing basic DEP concentration of bioparticles 302 within the field of view 304. (AC Voltage Source~100 KHz, 1V–500V) 303.

FIG. 3 shows the top view of a 4-electrode configuration that allows one to move the bioparticles inside the droplet. Once the bioparticle and medium are chosen, K(w) is fixed and the crossover frequency is fixed. The geometry of the electrodes and spacing and voltage applied determine the electric field lines. In the setup opposite electrodes have the same potential. The electrodes go outside the domain of the particle. This is done for two reasons: 1) a dry contact is possible between the electronic module and the electrodes and 2) there is only one region within the droplet where the electric field is minimum (the electric field between adjacent electrodes is maximum).

Figure 4:
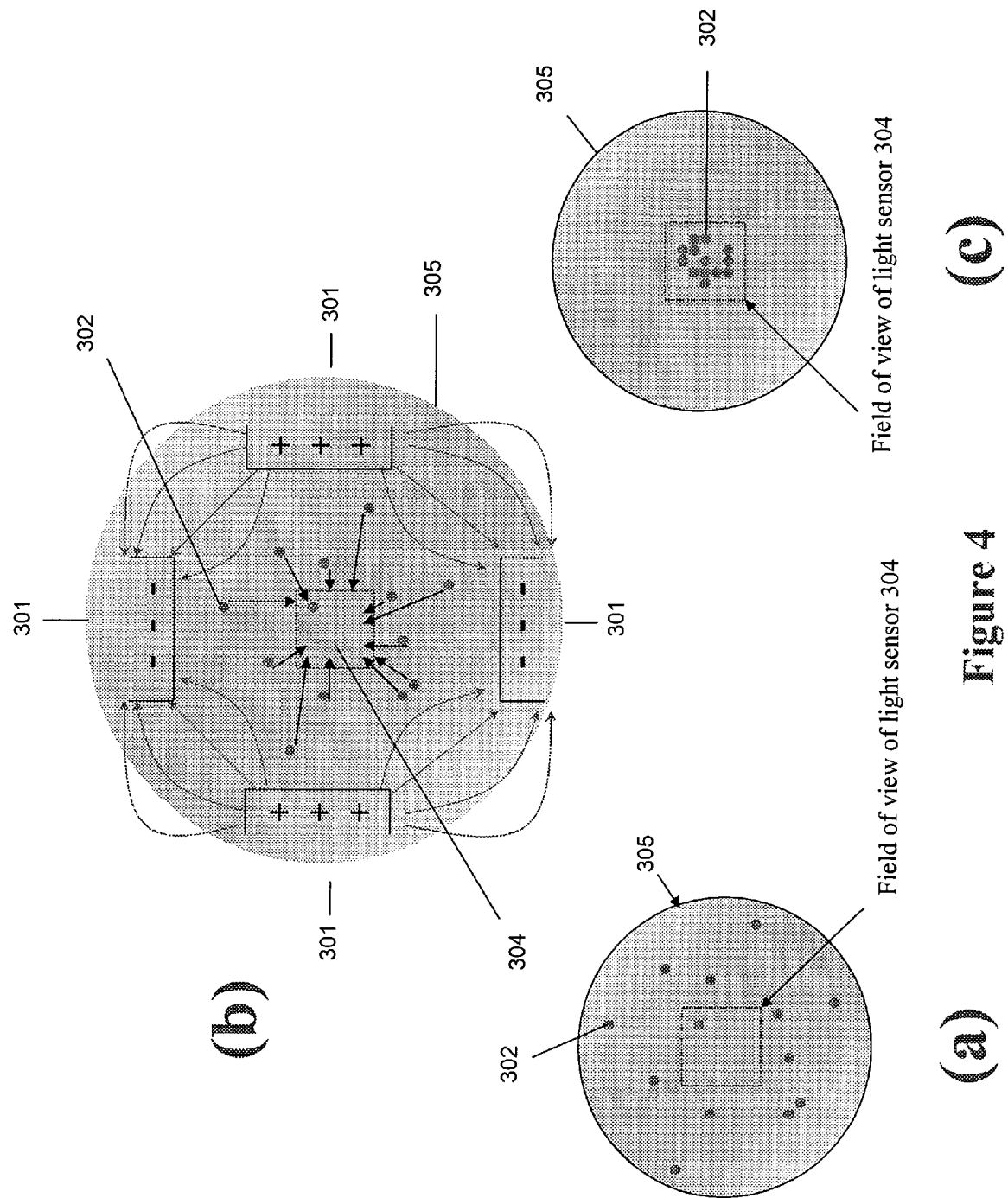
FIG. 4. (a) Distribution of the bioparticles 302 when no electric field 102 is applied. Lumen count=1 unit. (b) Movement of the bioparticles 302 towards the center of the electrode array 301 when an electric field 102 is applied. (c) Resulting clustering of all bioparticles 302 at the center of the electrode array 301. The electric field 102 has to be kept active to hold the bioparticles 302 in place. Lumen count=14 units.

Although FIG. 1b shows the distortion of the field lines by a particle, in reality the particles (<1 µm) are too small compared to the scale of the electrodes (100's of µm). The droplet usually covers an area of 100 µm×100 µm or more. This represents nanoliter quantities of the sample. So the distortion in the field lines due to the particles is not noticeable. FIG. 1c shows the field lines in a more realistic case. The region of maximum field gradient is between the adjacent electrodes. The region in the middle is the point of lowest field gradient. Hence when the applied frequency is lower than the crossover frequency, the bioparticles will experience positive dielectrophoresis and hence move to the periphery of the droplet to the region between the adjacent electrodes as shown in FIG. 4. However, when the frequency is increased beyond the crossover point, the bioparticles crowd in the center of the electrode array where the electric field gradient is minimum.

Fluorescence

Figure 5:
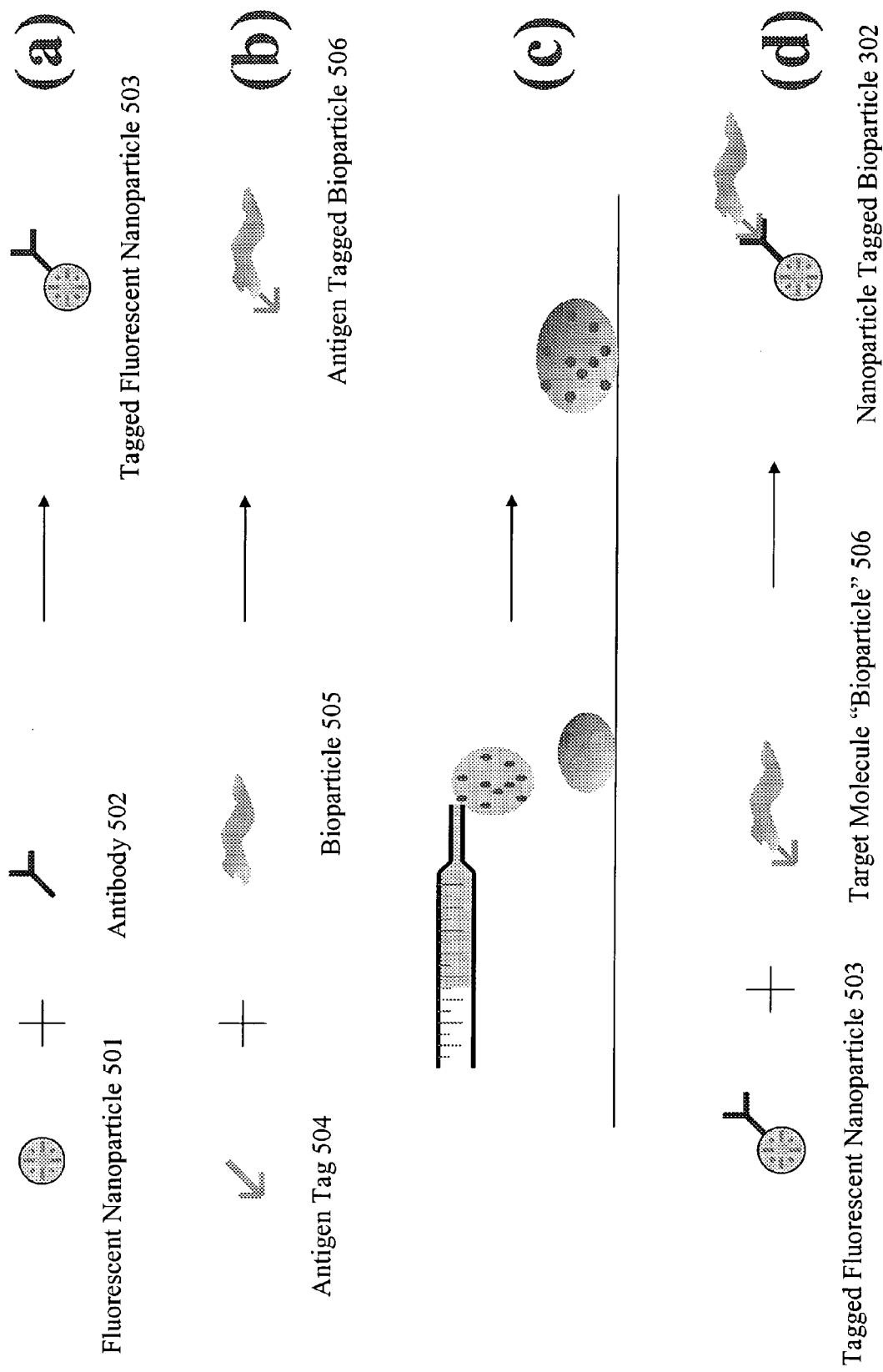
FIG. 5. (a) Tagging the fluorescent nanoparticle 501 with an antibody 502. (b) Tagging the bioparticle 505 with an antigen tag 504 (this step is optional as the antigen is already present in many cases). (c) Adding the reagent (tagged nanoparticle 503) to the tagged bioparticle 506. (d) Making the antigen—antibody link to attach the nanoparticle 503 to the bioparticle 506 (called "nanoparticle (NP) tagged bioparticle" 302).

Having gained the ability of positioning the particles, the particles can be detected by a low cost light detector. A fluorescent nanoparticle is attached to the bioparticle using an antigen—antibody connector. The nanoparticle is synthesized and then an antibody is attached to its surface (FIG. 5a). The bioparticle may display the antigen naturally or be the antigen itself. If a suitable antigen is not present, the bioparticle may be tagged with an antigen. The step shown in FIG. 5b is optional and performed if a suitable antigen is not present. The nanoparticles and bioparticles are placed together (FIG. 5c and FIG. 5d). The experiment should be designed in a manner in which the antibody-antigen bind specifically to each other and do not bind to other ingredients in the sample. The technology of this application may be utilized in cooperation with the technology included in the coassigned U.S. Provisional Patent Application No. 60/614,688, filed Sep. 30, 2004.

Figure 6:
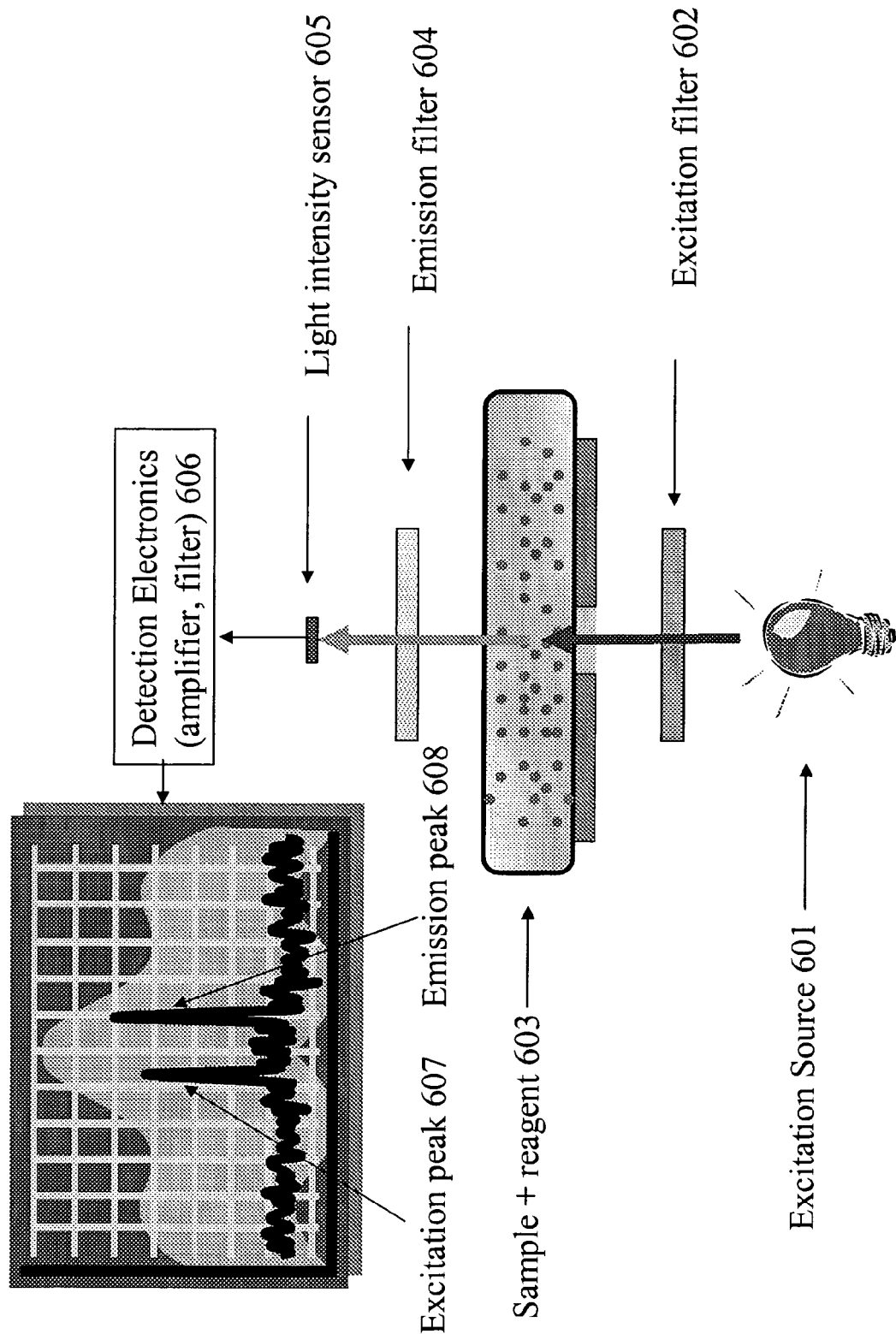
FIG. 6. Conventional fluorescence detection setup comprising an excitation source 601, excitation filter 602, sample and reagent 603, emission filter 604, light intensity sensor 605 and detection electronics 606. An excitation peak 607 and emission peak 608 are depicted.

FIG. 6 shows a procedure for detecting the bioparticles. An excitation source is provided in the bottom; an excitation filter ensures that the excitation wavelength is constrained. The drop is excited and the bioparticles in the sample emit radiation in the visible region. Larger fluoro-tags may be used (µm size beads). These types of tags are larger and less efficient in excitation to emission conversion. They are also plagued by quenching issues where the emission efficiency is diminished by tagging. Using nanoparticles as fluoro-tags provides much higher emission levels with minimal quenching. The emission is passed through another filter that selects a specific wavelength. Then a sensor (photodiode) measures the light output and converts it into a voltage or current.

Dielectrophoresis can be used to enhance detection accuracy and lower the cost of a bio-particle detection device. The bioparticle is attached to a nanoparticle based fluorescent tag. The use of the nanoparticle enhances the light output of the target hence raising its detectability.

Figure 7A:
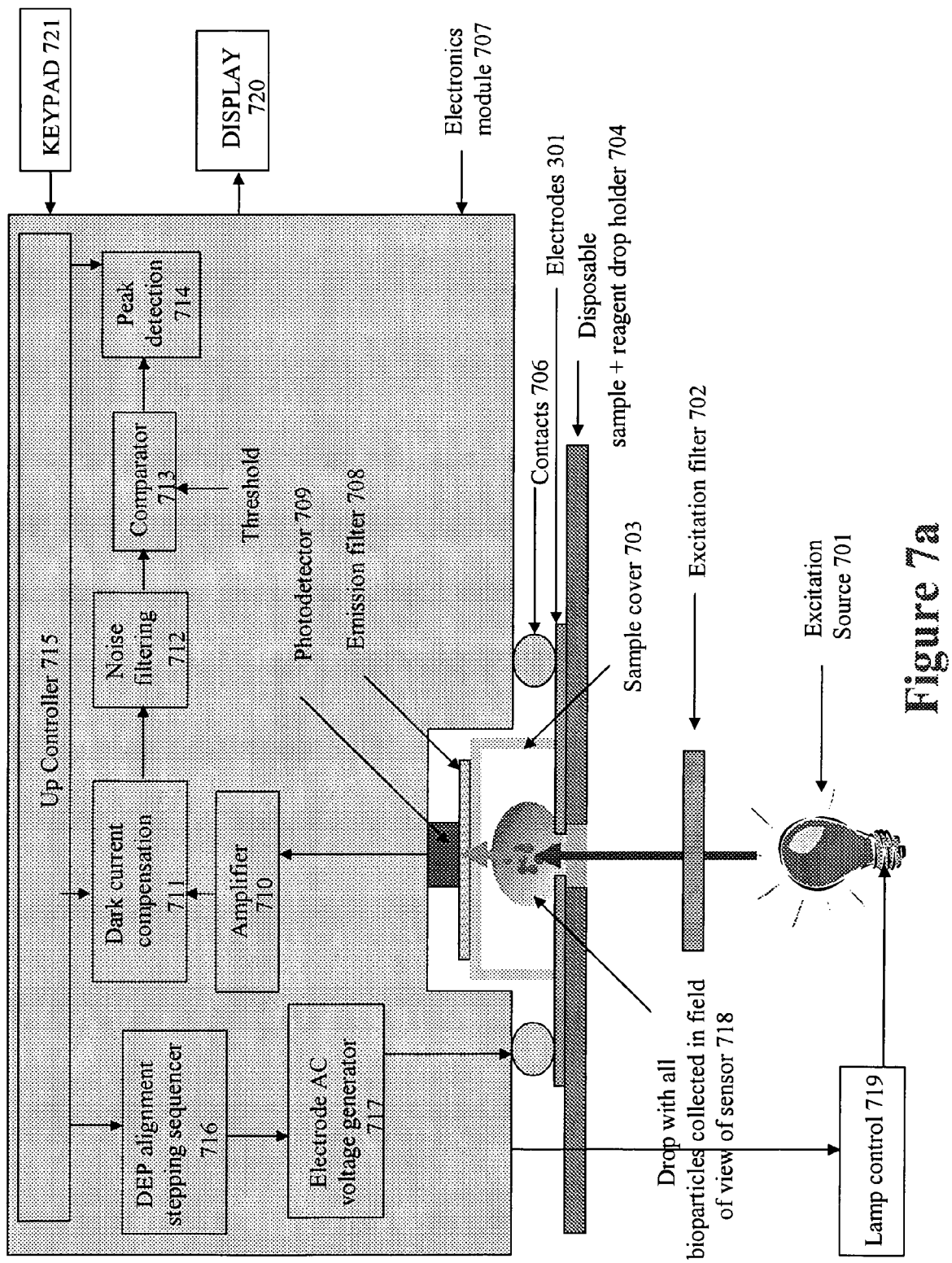
FIG. 7. (a) Setup described in an embodiment of this invention including an excitation source 701, excitation filter 702, sample cover 703, disposable sample and reagent drop holder 704, electrodes 301, contacts 706, electronics module 707, emission filter 708, photodetector 709, amplifier 710, dark current compensation 711, noise filtering 712, comparator 713, peak detection 714, up controller 715, DEP alignment stepping sequencer 716, electrode AC voltage generator 717, droplet 718, lamp control 719, display 720 and keypad 721. (b) Side view of an embodiment of the instrument.

The setup for detection uses a disposable sample holder. The reagents used to perform tagging are provided as a small drop to the sample holder. The sample and reagent constitute a small drop sitting in a small chamber in the sample holder. The sample holder can be made with glass, plastic or any other suitable material. Other materials can also be used, however, glass or plastic are low cost alternatives. In some embodiments, a printed circuit board material could also be used. Once the sample and reagents are delivered to the sample holder, a cover is provided for the sample holder to prevent evaporative loss of liquid. Electrodes are integrated on the sample holder for dielectrophoretic manipulation of the target particles (sometimes to move particles of no interest away from the detection field) in the drop. The electrodes may be in many shapes and patterns. They can be patterned by methods including but not limited to selective deposition or etching following blanket deposition. FIG. 7 shows the complete setup of the low cost fluorescence based bioparticle detection apparatus. Dielectrophoretic forces are utilized in bringing the particles into the field of the photodetector. Dielectrophoresis is also used for effective mixing of sample and reagent particles when combined.

In most analytical setups a provision is made for repeating the experiment under various emission wavelengths with emission measurements taken at each wavelength. While this is an elaborate process and of scientific interest, a low cost diagnostic instrument cannot afford to have these features. Linear array or imaging arrays are used to image the sample field. Linear scanning involves mechanical motion of the sample tray or the sensor. Imaging arrays are more expensive and involve the use of memory to create and store the image. Using optics to focus the droplet field can also add cost and size.

In a low cost rendering of a fluorescence measurement device (FIG. 7), a single photodiode can be used. The droplet size cannot be controlled and the position of the electrodes cannot be precisely positioned with regard to the detector. Moreover, if the detector is much smaller than the sample drop, alignment becomes an issue. The detector is placed very close to the sample to collect all the photons coming out of the sample. The tagged bioparticles should be directly in the field of maximum reception of the photodiode, when moved to the center of the electrode array using −ve dielectrophoresis.

The sample holder is usually a disposable glass slide. A cover slip is placed on the drop with or without deforming the drop. The electrodes are a part of the disposable holder as the sample makes contact with the electrode. A disposable system is required for contaminant free accurate results.

The K(w) term is used for determining the force experienced and the cross over frequency will change when the bioparticle gets tagged by the fluorescent nanoparticle (Eq. 1). Since the resulting tagged entity is actually two particles bridged by an antigen-antibody link, the K(w) of the combination should be determined by experimental techniques. If the bioparticle is in the μm size (as in cells or bacteria) then it would dominate the particle's permittivity. When viruses or DNA are tagged, the nanoparticle and the bioparticle are of comparable sizes. The need to identify the K(w) becomes important in order to design the crossover frequency so that the particle is always in the −ve dielectrophoresis region.

The sample may have more than one type of bioparticle. There may be other entities (of various sizes) in the sample. The sample could be simplified such that many interfering bioparticles are eliminated by high-speed spinning or other separation means. Some of these particles may and will move to the center or away from the center due to dielectrophoretic forces. Each one will have a different cross over frequency.

In a small domain like a micro drop, the presence of many colloidal particles in addition to the target bioparticle and the tagged nanoparticles present problems in detection. To improve detection: 1) The sample and reagents should be mixed well. Mixing samples in a cuvette is easy. Spinning and magnetic stirring techniques are known. But in a small nano-drop, new techniques are required. The success of tagging depends on whether each nanoparticles gets a chance (several) to collide with an unbound target bioparticle. 2) The small size of the sample allows quick evaporation. Loss of all liquid medium can render the test useless. Hence a lid or oil film is necessary to ensure integrity of the drop size. 3) When DEP is used to move the particles to the center, it is important to ensure that any other items that drift to the center a) do not clog or obstruct the tagged target particle from being excited, b) prevent the emitted light from reaching the detector, or c) block the tagged target from being aligned with the center.

While designing the procedure, it is beneficial to know what other particles are present and it is beneficial to remove undesired particles.

Efficient mixing of the sample and the reagent can be accomplished by changing the frequency of the applied electric field and moving the system from a +ve DEP mode to a −ve DEP mode and back to a +ve DEP mode. This can be repeated over several cycles. Alternating the modes makes the particles move from the center to the periphery. Introduction of a few dummy particles that move in the opposite direction of the bioparticle enhance the agitation. Another technique to accomplish mixing is to apply the electric field to only two adjacent electrodes at a time and cycle through each adjacent pair.

This photodetector provides the desired sensitivity for the detection of very small quantities of bioparticles in nanoliter quantity of sample. The photodetector is small and sensitive. The detector is mounted very close to the sample. In one embodiment, it actually makes contact with the cover for the sample holder. The close proximity of the photodetector ensures that almost all photons emitted from the top of the sample holder are collected by the photodetector. A smaller photodetector gives better detection accuracy because of lower detector noise and dark current. Use of a smaller area photodiode is possible when one has the means to concentrate the fluorescent particles under the electrode. FIG. 4 depicts how to perform this concentration. An advantage of using a cover for the sample drop is that the photodetector is separated from the sample as the photodetector is not part of the disposable entity.

Figure 9:
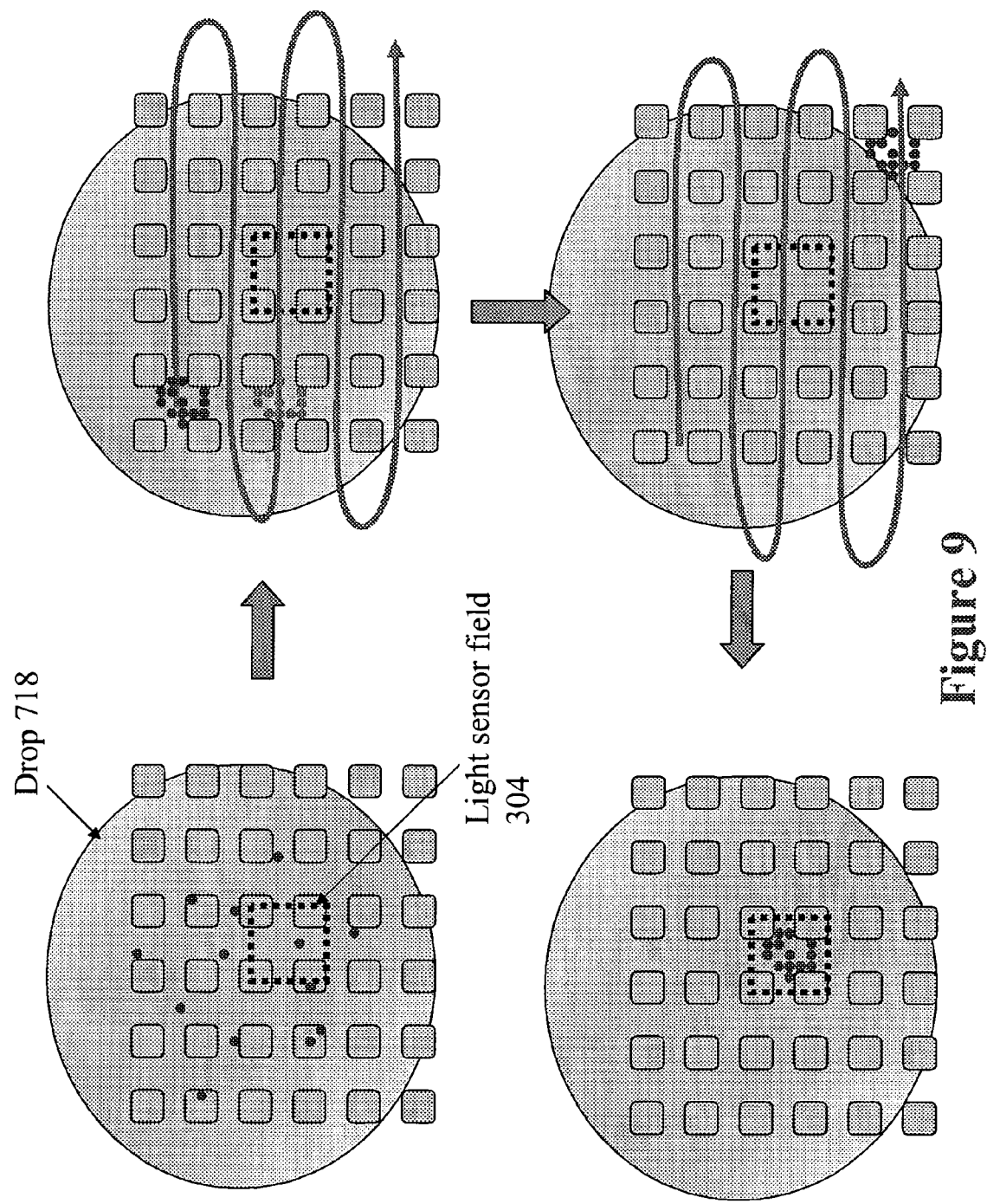
FIG. 9. Using an array of electrode 301 to position the NP tagged bioparticle 302 cluster to the center of the photodetector field of view 304. Initially all NP tagged bioparticles 302 are scattered throughout around the drop 718. All tagged bioparticles 302 are collected at start of scanning path. NP tagged bioparticles 302 are moved from one site to the next along the scanning path. At the end of the scan, the position of maximum detector output is determined. All NP tagged bioparticles are collected under the light sensor field 304.
Figure 10:
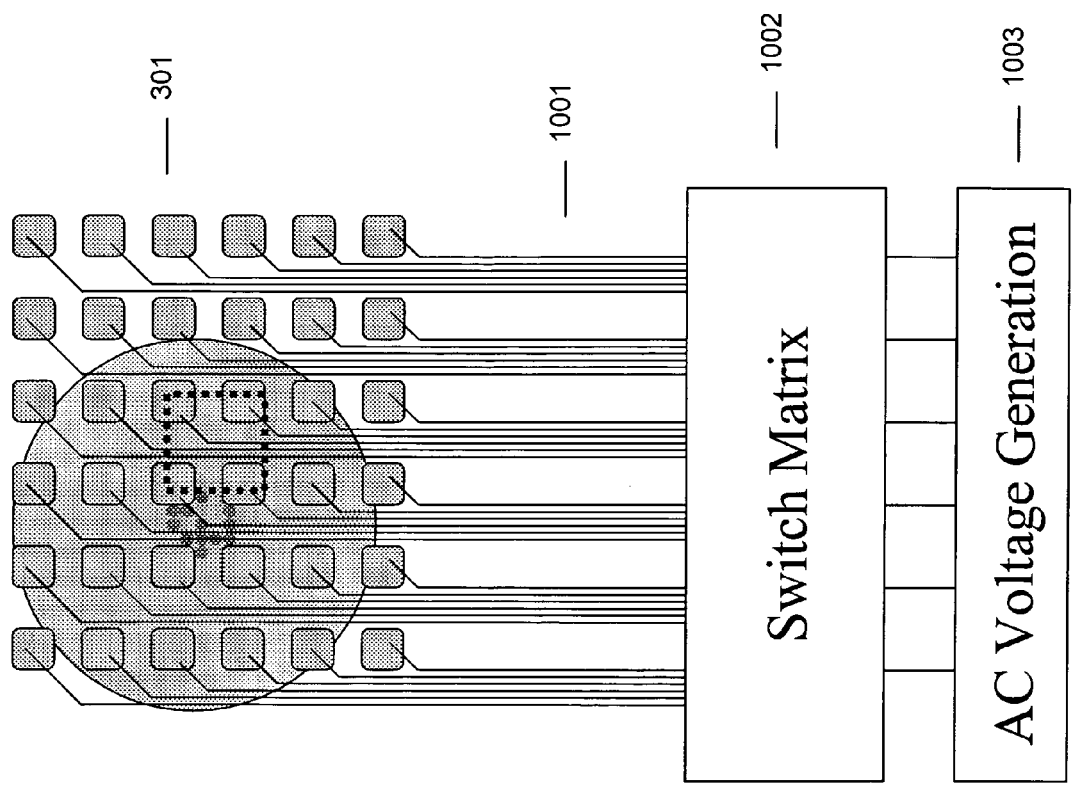
FIG. 10. Wiring 1001, switch matrix 1002 and AC voltage generation 1003 for controlling the electrode array 301.

Usually the drop spreads over an area of 2 mm×2 mm. While the detector is around 20 μm×100 μm. Hence it is important to ensure that the point of concentration of the fluorescent particles is directly under the photodetector. Ensuring such fine alignment by construction is difficult as the two items in question are movable parts. FIG. 9 shows how dielectrophoresis can be used to place the fluorescent particle cluster at several points on a scanning path. One of these points will bring it directly under the field of view of the photodetector. An array of electrodes is present inside the drop (the array can also be below the drop, in which case, a small transparent insulating layer would separate the liquid from the electrode). The electrodes are fed different AC voltages in a desired sequence. FIG. 10 shows the wiring and the switch matrix used to apply different voltages to different electrodes in the array. A microprocessor or microcontroller in the electronics module generates the sequence and switch control signals.

In an alternate embodiment, a calibration step can be used when it is possible to locate the position where the particle cluster of a calibration particle set aligns itself best and to use the same electrode voltage setting for future tests.

The UV source (or excitation source) can be placed below the sample holder. This requires that the sample holder be transparent to UV. The cover used for the sample should be transparent to visible light. In an alternate embodiment, the UV source can be placed on the same side, but this requires that the photodetector be raised a little so that the UV excitation may strike the sample. This reduces the efficiency of photon collection. An emission and excitation filter may be optionally used based on the type of the excitation source and detector.

The electronics are housed either in integrated form or in discrete form (built out of individual components available in the market) in a separate module called the electronics module. Contact is made between the electronics module and the sample holder at the far end of the electrodes as shown in FIG. 7. Spring-loaded bumps (contacts) are placed in the module for making efficient contact with the electrodes.

Figure 7B:
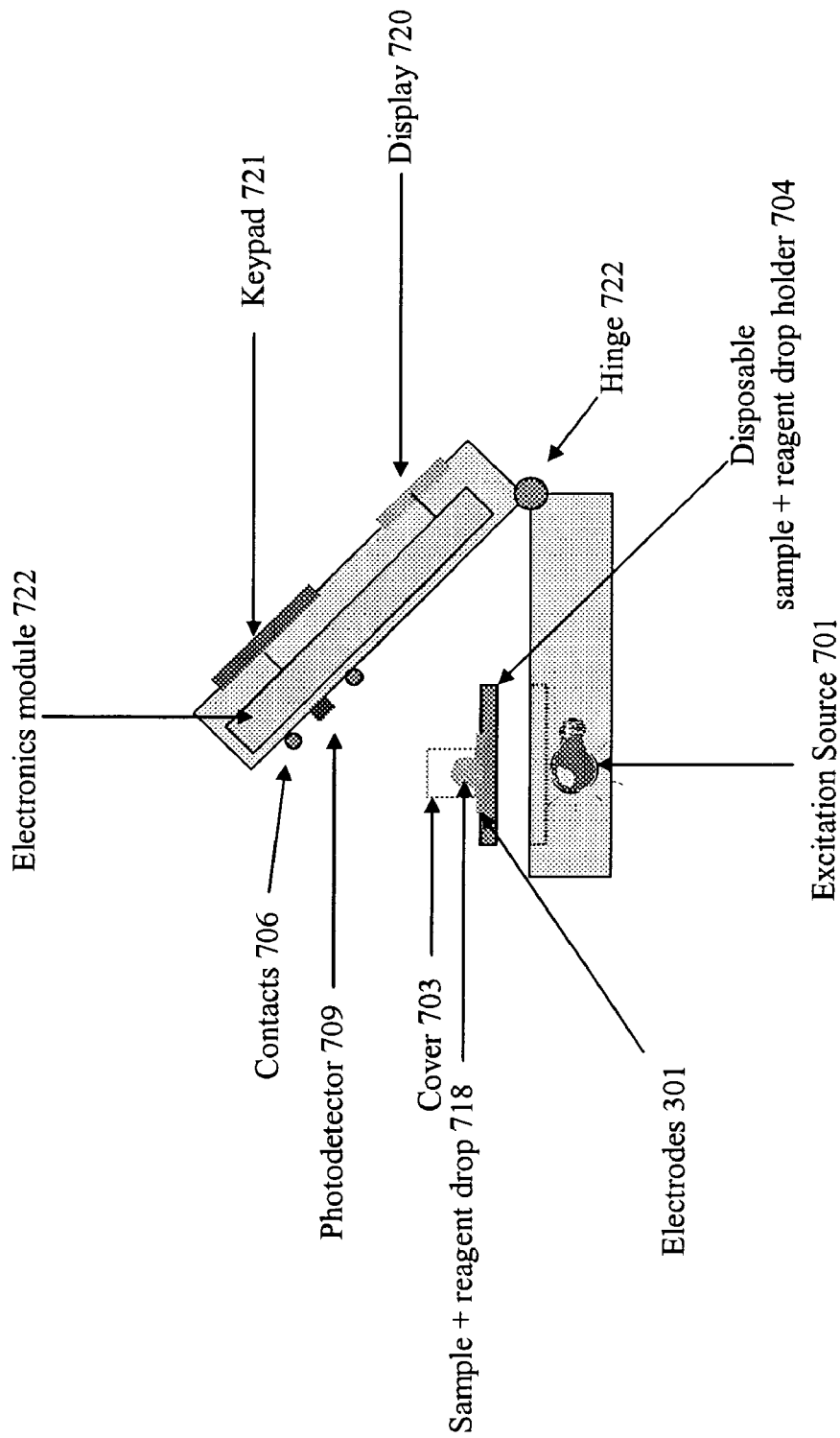
Figure 8A:
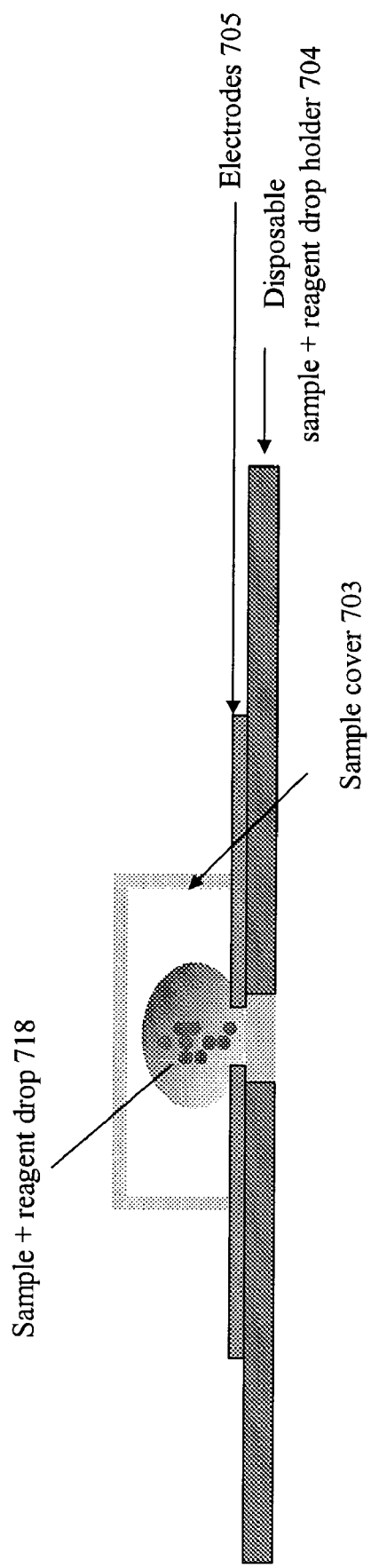
FIG. 8. (a) Side view of the disposable sample holder. (b) Top view of the disposable sample holder.
Figure 8B:
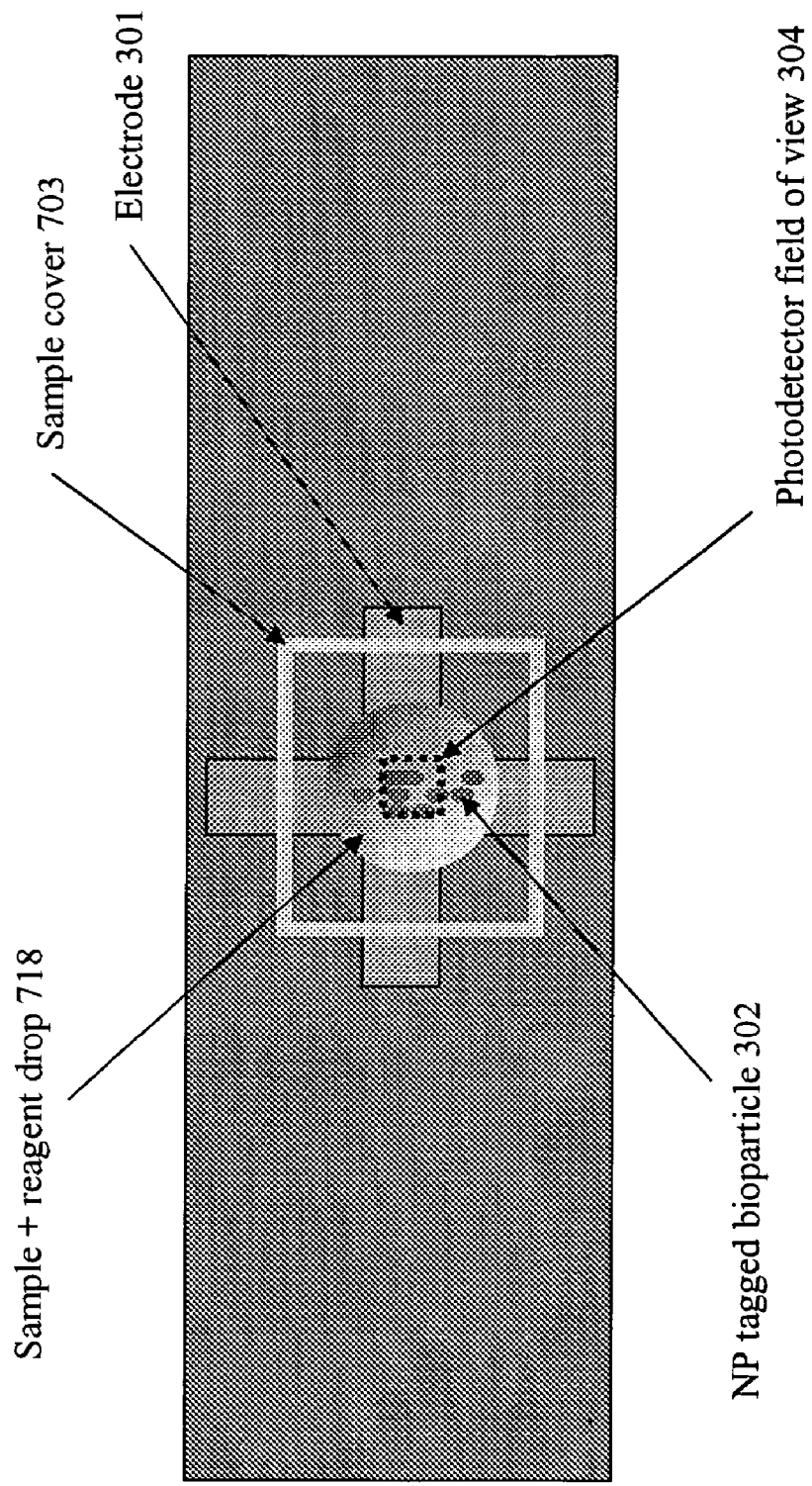

Contact is made when the sample holder is loaded into the detection instrument. Various mechanisms can be envisioned for the purpose. The construction of the instrument may be in two parts as shown in FIG. 7b. The top part houses the electronics module, the detector assembly, the calibration and computation electronics, and the display. The bottom part can house the UV source (or excitation source) and power supply. The bottom part can also have a groove for placing the disposable sample strip.

In most inventions relating to the use of "lab-on-a-chip", the electronics are combined with the electrodes. An embodiment of the present apparatus does not integrate the electronics with the electrodes in order to reduce cost. Separating the electronics allows the disposable part to be very low cost. It provides freedom in choosing the materials for the sample holder. When electrode spacing of very fine dimensions is necessary, silicon can be used as the core of the sample container. However, no electronic devices are integrated on the silicon. Silicon is used because metal electrodes can be fabricated on silicon at much higher precision in comparison to printing electrodes on plastic or glass.

The single sample version described above may be extended to a array of sample pits for conducting experiments in parallel. If an array of sample pits are used, an array of photodetectors will be useful to image all the sample pits. Another possibility is to use a single photodetector and move it with micron precision from one to the next. Electronics may be integrated on the sample holder. In one embodiment where there is large array of sample pits and individual ones have to be addressed, it would not be efficient to use contacts from the top unit. An addressing mechanism would be used. These embodiments would provide an increased cost. In a majority of the applications, single sample holders are adequate. These extensions are not directed toward low cost detection.

Another feature commonly used in "lab-on-a-chip" is to fix reagent molecules to the base of the sample holder. Several sample pits with unique predetermined reagents attached to the bottom of the sample pits are fabricated so that multiple tests can be performed on the same sample holder. Similar methods to those above may be used.

Sample and reagent may be delivered manually to the sample pit. This makes the sample holder general purpose without the need to customize for any particular test.

In other diagnostic equipment, the detection is done using electrical conductivity change. While it does not require optics and an optical detector, it cannot avail of the advantages of fluorescent nanoparticles. Moreover the electrode assembly becomes more complex. In the present apparatus, electrical conductivity is not used as a detection mechanism.

Advantages

The apparatus and method works on small quantities, for example, 0.01-1 nanoliter drops. If a larger sample size is available then the solution can be concentrated using a spinning or evaporative technique to increase sample concentration. If the sample concentration is high then the advantage of this technique is that it can be repeated several times as the amount required per test is very little.

The disposable part of the test may be a glass or plastic slide that has only the sample well and the electrodes. It does not contain the electronics. Adding electronics increases the cost of the disposable item. An electronic unit is used to generate the AC voltage of the right frequency and voltage to be applied through contact electrodes to the electrodes on the sample holder. The electronic unit being non-disposable helps in lowering cost of parts and calibration. A cutout is provided in the electronic unit for the imaging to work.

Use of –ve dielectrophoresis by applying the suitable AC voltage and frequency at the electrodes to move all the luminescent bioparticles to the center of the field of view of the sensor.

Using a multiple electrode array to position the cluster of fluorescent particles to the center of the detector field. The multiple electrode array allows one to change to point of maximum/minimum electric field so the particles can be moved to the desired location.

Using a sequence of electrode potentials to position the fluorescent particles at various points with regard to the detector in order to search for point of maximum detector output. Since the starting location of the particles is not known with regard to the detector, an automatic search algorithm is utilized to find the optimum positioning. Manual alignment is slow and would require optics which would add cost.

The use of a larger nanoparticle to increase the Claus Mosetti factor so that the AC voltage and frequency at which DEP sets in is convenient for low cost generation using electronic components. Generating 1 V is generally easier and safer than generating and applying 100 V to the electrodes.

Using the right coating on the sample container (glass or plastic slide) such that the surface tension is adjusted so that the droplet is as flat as possible to increase the detection efficiency. The flatter the droplet, the lesser the effect of the droplet optical effects on the imaging.

Using a switching pattern to the electrodes so that the sample reagent mixture gets thoroughly mixed to ensure completed target particle tagging.

An alternative way of stirring is to added inert magnetic nanoparticles to the drop and stir the mixture by phasing a magnetic field under the sample holder. This approach adds two cost factors—magnetic NP and a phasing magnetic filed generation.

Evaporation is prevented by using a cover slip that is sealed on the drop after reagent delivery. The cover may or may not flatten the drop. Alternatively, an oil film on the drop can be used to avoid evaporation.

An opening is built in the electronics module so that the emitted light is delivered to the detector. Alternatively, the detector can be mounted on the underside of the electronic module and the emission filter (optional) may be fabricated as a layer on the photodiode during manufacture.

Using a suitably chosen crossover frequency (done by adjusting medium concentration and conductivity) so that only the tagged bioparticles moves to the center (by experiencing –ve DEP) and the rest of the non-target bioparticles move to the vicinity of the electrodes by +ve DEP.

Placing two photodetectors, one above and one below the sample so that the photon collection efficiency is double. The outputs of the two detectors can be added.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. It is therefore, contemplated that the claims will cover any such modifications or embodiments that fall within the true scope of the invention.

REFERENCES

All publications and patent applications mentioned in this specification are indicative of the levels of those skilled in the art to which this invention pertains. All publications and patent applications are herein incorporated by reference to the same extent as if each individual publication or patent application was specifically and individually indicated to be incorporated by reference.

(1) Methods of Analysis/Separation, A. Parton et. al, U.S. Pat. No. 5,999,631, Nov. 30, 1999.

(2) Dielectrophoretic Concentration of particles under electrokinetic flow, R. R. Miles et. al, U.S. Pat. No. 6,787,018, Sep. 7, 2004.

(3) Method and apparatus for dielectrophoretic manipulation of chemical species, J. S. Batchelder, U.S. Pat. No. 4,390,403, Jun. 28, 1983.

(4) Method of continuously separating mixtures of microscopic dielectric particles and apparatus for carrying through this method, W. Benecke, et. al. U.S. Pat. No. 5,454,472, Oct. 3, 1995.

(5) Process for manipulating microscopic, dielectric particles and a device therefore, W. Benecke, et. al., U.S. Pat. No. 6,149,789, Nov. 21, 2000.
(6) Process and device for generating resonance phenomenon in a particle suspensions, G. Fuhr, et. al, U.S. Pat. No. 6,056,861, May 2, 2000.
(7) Apparatus for switching and manipulating particles and method of use thereof, X. Wang, et. al., U.S. Pat. No. 6,596,143, Jul. 22, 2003.
(8) Active programmable electronic devices for molecular biological analysis and diagnostics, M. J. Heller, et. al, U.S. Pat. No. 5,605,662, Feb. 25, 1997.
(9) Molecular Biological diagnostic systems including electrodes, M. J. Heller, et. al., U.S. Pat. No. 5,632,957, May, 27, 1997.
(10) Nanoelectromechanics in engineering and biology, M. P. Hughes, CRC Press.
(11) Detection of target analytes using particles and electrodes, C. C. Bamdad, et. al, U.S. Pat. No. 6,541,617, Apr. 1, 2003.
(12) In situ assembly of Colloidal particles into miniaturized biosensors, O. D. Velev, and E. W. Kaler, Langmuir, Vol. 15, No. 11, pp. 3693-3698, May 25, 1999.
(13) Towards single molecule manipulation with dielectrophoresis using nanoelectrodes, L. Zheng, et. al., Proceedings of the 3rd IEEE Conference on Nanotechnology, 1, 437-440 (2003).
(14) Control and modeling of the dielectrophoretic assembly of on-chip nanoparticle wires, K. H. Bhatt, O. D. Velev, Langmuir, Sep. 24, 2004, Vol. 20, No. 2, pp. 467-476.
(15) Working with FluoSpheres Fluorescent Microspheres, June 2004, Molecular Probes, www.probes.com.
(16) TD700 Laboratory fluorometer, www.turnerbiosystems.com.

What is claimed is:

1. An apparatus for detection of bioparticles comprising:
   (a) an excitation source;
   (b) a disposable sample holder comprising electrodes, wherein the disposable sample holder is situated to receive output from the excitation source;
   (c) a sample in form of a drop comprising bioparticles, wherein the drop is situated on the disposable sample holder;
   (d) an AC voltage generator located in contact with the electrodes; and
   (e) a photodetector disposed to receive fluorescence from the bioparticles on the disposable sample holder, wherein the apparatus is operable to use dielectrophoresis to concentrate bioparticles in the drop into the field of view of the photodetector.

2. The apparatus of claim 1, further comprising an excitation filter located between the excitation source and the sample.

3. The apparatus of claim 1, further comprising an emission filter located between the sample and the photodetector.

4. The apparatus of claim 1, further comprising a sample cover located between the sample and the photodetector.

5. The apparatus of claim 1, further comprising a multiple electrode array, wherein the multiple electrode array is operable for bringing a tagged bioparticle cluster into the field of view of the photodetector.

6. The apparatus of claim 1, wherein the sample comprises tagged bioparticles.

7. The apparatus of claim 1, further comprising a fluorescent nanoparticle tagged with an antibody, wherein the fluorescent nanoparticle is operable for detecting the bioparticles in the sample.

8. The apparatus of claim 1, wherein the apparatus is operable for using a switching pattern to mix the sample.

9. The apparatus of claim 1, wherein the apparatus is operable to utilize dielectrophoresis at a proper crossover frequency so that only the tagged bioparticles move into the field of view of the photodetector.

10. A method for detection of bioparticles comprising:
    (a) adding a fluorescent nanoparticle tagged with an antibody to a sample;
    (b) placing the sample in the form of a drop comprising bioparticles upon a disposable sample holder;
    (c) placing the disposable sample holder comprising electrodes in contact with an AC voltage generator;
    (d) using dielectrophoresis to concentrate tagged bioparticles in the drop into the field of view of a photodetector;
    (e) exposing the bioparticles in the drop upon the disposable sample holder to an excitation source; and
    (f) detecting fluorescence of the tagged bioparticles in the drop.

11. The method of claim 10, further comprising using an excitation and an emission filter.

12. The method of claim 10, further comprising using an amplifier.

13. The method of claim 10, further comprising covering the sample with a sample cover.

14. The method of claim 10, further comprising using a multiple electrode array to bring a tagged bioparticle cluster into the field of view of the photodetector.

15. The method of claim 10, wherein a switching pattern is used to mix the sample.

16. The method of claim 10, further comprising selecting a proper crossover frequency so that only the fluorescent nanoparticle tagged bioparticles move into the field of view of the photodetector.

17. An apparatus for detection of bioparticles comprising:
    (a) an excitation source;
    (b) a disposable sample holder comprising electrodes, wherein the disposable sample holder is situated to receive output from the excitation source;
    (c) a sample in the form of a drop comprising bioparticles, wherein the drop is situated on the disposable sample holder;
    (d) an AC voltage generator located in contact with the electrodes; and
    (e) a photodetector disposed to receive emission from the bioparticles on the disposable sample holder, wherein the apparatus is operable to use dielectrophoresis to concentrate bioparticles in the drop into the field of view of the photodetector.

* * * * *